(12) United States Patent
Sabourin (10) Patent No.: US 11,613,293 B2
(45) Date of Patent: Mar. 28, 2023

(54) CAPACITIVE DEVICE FOR DETECTING THE PRESENCE OF A PERSON CLOSE TO OR IN CONTACT WITH A COMPONENT OF A MOTOR VEHICLE

(71) Applicant: Autoliv Development AB, Vargarda (SE)

(72) Inventor: Pierre Sabourin, Ecquevilly (FR)

(73) Assignee: Autoliv Development AB

( * ) Notice: Subject to any disclaimer, the term of this patent is extended or adjusted under 35 U.S.C. 154(b) by 65 days.

(21) Appl. No.: 17/255,139

(22) PCT Filed: Jun. 19, 2019

(86) PCT No.: PCT/EP2019/066177
§ 371 (c)(1),
(2) Date: Dec. 22, 2020

(87) PCT Pub. No.: WO2020/002079
PCT Pub. Date: Jan. 2, 2020

(65) Prior Publication Data
US 2021/0270637 A1 Sep. 2, 2021

(30) Foreign Application Priority Data
Jun. 27, 2018 (FR) ...................................... 1855743

(51) Int. Cl.
*G01R 27/26* (2006.01)
*B62D 1/04* (2006.01)
(Continued)

(52) U.S. Cl.
CPC ............. *B62D 1/046* (2013.01); *B60N 2/002* (2013.01); *B62D 15/021* (2013.01); *G01D 18/00* (2013.01); *G01D 5/24* (2013.01)

(58) Field of Classification Search
CPC ........ G01D 5/24; B60N 2/002; B62D 15/021; G01R 27/26
(Continued)

(56) References Cited

U.S. PATENT DOCUMENTS

2015/0367751 A1 12/2015 Lamesch et al.
2017/0355337 A1 12/2017 Lamesch
(Continued)

FOREIGN PATENT DOCUMENTS

EP          0802420 A2   10/1997
WO     2016/055667 A1    4/2016

*Primary Examiner* — Vincent Q Nguyen
(74) *Attorney, Agent, or Firm* — Matthew D. Thayne; Thayne and Davis LLC (57) ABSTRACT

A capacitive detection device that may include at least one electrode of a capacitive sensor, an alternating voltage source, a device for measuring a complex value of impedance or admittance between the detection electrode and an electrical circuit reference point and a calibration resistor, and a switching device arranged so as to connect the voltage source to the electrode, in the measurement mode, and to connect the voltage source to the calibration resistor and disconnect the voltage source from the electrode, in the calibration mode. The measuring device is arranged so as to measure a first complex value of the calibration resistor, during operation in the calibration mode; to measure a second complex value between the electrode and the electrical circuit reference point during operation in measurement mode, and to correct the second measured complex value according to the first measured complex value.

17 Claims, 5 Drawing Sheets

(51) Int. Cl.
  *B60N 2/00* (2006.01)
  *B62D 15/02* (2006.01)
  *G01D 18/00* (2006.01)
  *G01D 5/24* (2006.01)

(58) Field of Classification Search
  USPC .............................. 324/601, 658, 660–663
  See application file for complete search history.

(56) References Cited

U.S. PATENT DOCUMENTS

2018/0037137 A1\* 2/2018 Goedert ................ B60N 2/002
2019/0226879 A1\* 7/2019 Lakatos ................ B62D 1/046

\* cited by examiner

CAPACITIVE DEVICE FOR DETECTING THE PRESENCE OF A PERSON CLOSE TO OR IN CONTACT WITH A COMPONENT OF A MOTOR VEHICLE

The present invention relates in general to a capacitive detection device for a motor vehicle intended for detecting the presence of a person close to or in contact with a component of the vehicle. The device can be used in particular to detect the presence of the hands of a driver on the steering wheel of the vehicle or the presence of an occupant on one of the seats of the vehicle.

Such capacitive devices are known from the prior art, in particular from document US 2015/0367751 which describes a capacitive device for detecting the presence of a person on a vehicle seat. The capacitive device described in US 2015/0367751 comprises an "antenna" electrode or "detection electrode" arranged in the seat, an alternating voltage source and a current measurement circuit. The alternating voltage source and the current measurement circuit are connected to the antenna electrode. A frame portion of the seat, connected to the frame ground of the vehicle, serves as a second electrode coupled to the antenna electrode so as to form a capacitive sensor. The measurement of a complex impedance between the antenna electrode and the frame ground of the vehicle makes it possible to detect the presence of a person on the seat. The capacitive device also comprises a known normative impedance coupled to a switching element. During operation in measurement mode, the current measurement circuit measures the alternating current circulating between the antenna electrode and the frame ground and at the input of a transimpedance operational amplifier OP AMP having a current-voltage converter function. The sought complex impedance between the antenna electrode and the frame ground can be calculated from an output voltage of the transimpedance amplifier, from the complex output signal of the voltage source and from a proportionality factor α. In order to determine or remove this proportionality factor α, the measurement taken in measurement mode is repeated during an operation of the capacitive device in calibration mode. In calibration mode, the normative impedance is switched electrically in parallel with the impedance to be determined between the antenna electrode and the frame ground. This sought impedance between the antenna electrode and the frame ground is then calculated from the complex output voltages of the transimpedance amplifier measured in measurement mode and in calibration mode and from the normative impedance.

Document US 2017/355337 describes a complex impedance measurement circuit for a capacitive sensor with two electrodes. In order to calculate the absolute values of the real and imaginary portions of the complex impedance of the capacitive sensor, an operation of amplitude normalization and phase correction is carried out by multiplying the real portion and the imaginary portion of the measured complex impedance by a calibration vector determined beforehand.

However, the prior art does not make it possible to measure a complex impedance or admittance with precision. The present invention aims to improve the situation. To this end, the invention relates to a capacitive detection device for detecting the presence of a person close to or in contact with a component of a motor vehicle, provided with a capacitive sensor, said device comprising at least one electrode of the capacitive sensor,
a voltage source arranged to supply an alternating voltage,
a device for measuring a complex value, corresponding to an impedance or an admittance, between said electrode and an electrical circuit reference point;
a calibration resistor for calibrating the measurement of a complex value of impedance or admittance.

The electrode of the capacitive detection device belongs to a capacitive sensor provided on the component of the vehicle close to or in contact with which presence of a person is to be detected. The capacitive sensor comprises two electrodes separated by a dielectric material.

Advantageously, the capacitive detection device comprises one of the two electrodes of a capacitive sensor and the component of the vehicle comprises the other electrode of the capacitive sensor.

Advantageously still, at least one of the electrodes of the capacitive sensor can be embodied by a structural element of the vehicle component. For example, such an electrode can be embodied by an armature element of the vehicle component. Said capacitive detection device is characterized in that it comprises a switching device arranged to:

connect the voltage source to said electrode, in measurement mode,
connect the voltage source to the calibration resistor and disconnect said electrode from the voltage source, in calibration mode,
and the measuring device is arranged to:
measure a first complex value of the calibration resistor, during operation in calibration mode;
measure a second complex value between said electrode and the electrical circuit reference point, during operation in measurement mode, and
correct the second measured complex value based on the first measured complex value.

Thus, in calibration mode, the voltage source is connected selectively to the calibration resistor and disconnected from the electrode. Optionally, when the voltage source is connected to the electrode, it can be disconnected from the calibration resistor. The calibration resistor, whose resistive value is determined (calibrated) and known, is used to measure a complex impedance or admittance during operation in calibration mode (in other words by switching the voltage source only to said calibration resistor). The measured complex value (of impedance or admittance) of the calibration resistor makes it possible to rectify the measurement of the sought complex value of impedance or admittance (between the detection electrode and the frame ground) measured by the measuring device in measurement mode (that is by switching the voltage source to the electrode). The invention makes it possible, by this calibration system, to effectively compensate for any drift in the measurement due to climate variations (temperature and humidity in particular) or to take into account the operating variables of the electronic components used for manufacturing the device. In a specific embodiment of the invention, the capacitive detection device comprises two calibration resistors.

Using two calibration resistors makes it possible to take two measurements of complex values of impedance or admittance of two electric dipoles having different resistive values. Two different measurement points are thus obtained in a complex plane (of impedance or admittance).

In a first embodiment, the two calibration resistors have different resistive values. In this case, the device separately measures the complex value (of impedance or admittance) of each of the two calibration resistors. Advantageously, the two calibration resistors are mounted in parallel and the switching device is arranged to connect the voltage source selectively to one or the other of the two calibration resistors.

For example, a first one of the calibration resistors has a resistive value comprised between 1 kn and 20 kn, preferably between 5 kn and 15 kn, and a second one of the calibration resistors has a resistive value comprised between 10 kn and 200 kn, preferably between 50 kn and 150 kn. These two ranges of values are defined to be close to the complex value of impedance added by two hands on the steering wheel and to the complex value of impedance added by one finger on the steering wheel, respectively.

In a second embodiment, the two resistors are identical. In this case, the device measures, for example, the complex value of impedance or admittance of only one of the two calibration resistors and the complex value of impedance or admittance of the two calibration resistors mounted in series or in parallel.

In any case, obtaining two separate calibration measurement points corresponding to two electric dipoles having different resistive values makes it possible easily to correct the phase of the measurement since the two complex values of calibration measured must necessarily be aligned with the zero of the complex plane of impedance or admittance.

Advantageously, the measuring device is arranged to apply an offset correction to the second measured complex value, said offset correction corresponding to a translation according to a vector $\overrightarrow{S_{OC}O}$ in a complex plane, the point $S_{OC}$ being a point of the complex plane corresponding to an open-circuit complex value of admittance or impedance of the capacitive detection device and the point O corresponding to the origin of the complex plane. The offset correction makes it possible to correct certain interfering effects of the different stages of the emitting or receiving electronics as well as of the connection cables of the capacitive detection device on the measurement of complex impedance. The present invention thus makes it possible to guarantee that the measurements of complex impedance are zero.

Advantageously still, the measuring device is arranged to calculate said open-circuit complex value of impedance or admittance of the capacitive detection device from two complex values measured by means of the two calibration resistors. The device for measuring complex impedance can be arranged to measure an open-circuit complex value (of impedance or admittance) and to compare said measured open-circuit complex value and the calculated open-circuit complex value (of impedance or admittance) in order to verify the correct operation of the capacitive detection device.

Advantageously still, the measuring device is arranged to apply a phase correction to the second measured complex value, said phase correction corresponding to a rotation according to an angle α between a straight line defined by two points in a complex plane, obtained from two complex values of impedance or admittance measured by means of the two calibration resistors, and an axis of the resistances or conductances of the complex plane. "Calibration resistors" is understood herein to refer to two resistors having known resistive values or optionally one resistor having known resistive value and one resistor of infinite value equivalent to an open circuit. The resistors are chosen to have a more precise resistance value (of the order of 0.1%) than the rest of the other components. They are also chosen to have a very low temperature drift (of the order of 15 ppm) and/or better resistance to mechanical or thermal stress. They can, for example, use "thin film" technology, which makes it possible to obtain better performance than the "thick film" technology that is commonly used. Indeed, a resistor using "thick film" technology changes more considerably when passing through a furnace.

Advantageously, the measuring device is arranged to apply at least one of the two corrections comprising an offset correction and a phase correction, as previously defined. In other words, the measuring device can be arranged to apply either an offset correction, or a phase correction, or an offset correction and a phase correction.

Advantageously still, the capacitive detection device comprises a pair of protective capacitors in series, said pair of capacitors being mounted in parallel with the one or more calibration resistors and one of the two capacitors is connected at its terminals to the voltage source via two respective switches and the other capacitor is connected to a frame ground of the vehicle. The protective capacitors make it possible to protect the calibration resistors, which are preferably precision resistors that are more sensitive than conventional resistors, against the effects of ESD (electrostatic discharge). Advantageously, the capacitive values of the protective capacitors are chosen in ranges close to the values of the design capacitances of the capacitive detection device. Thus, the currents measured in calibration mode are similar to those measured in measurement mode. This guarantees an optimal measurement precision.

The capacitive detection device can be arranged to repeat the measurement of the second complex value between the electrode and an electrical circuit reference point cyclically and, between two consecutive measurements of said second complex value, to take a single calibration measurement.

Previously, during an initial calibration phase, the device can be arranged to take two calibration measurements of a first complex value of impedance or admittance of two different electric dipoles produced from the two calibration resistors.

The invention thus makes it possible to guarantee a continuous calibration over time of the measurement of complex impedance and to continuously compensate for any possible interfering effect (for example the temperature), without degrading the rhythm of the measurements of the complex impedance between the electrode and the electrical circuit reference point.

Advantageously, the measuring device is arranged to calculate a capacitance value between the electrode and an electrical circuit reference point of the vehicle, from said second complex value (of impedance or admittance) measured and then corrected, by applying a scaling gain G to the imaginary portion of said second complex value measured and then corrected, the gain G being provided by the equation $$G = \frac{|R_{C1} - R_{C2}|}{R_{C1} \times R_{C2} \times \|\overrightarrow{C_{R\_C1}C_{R\_C2}}\|}$$

wherein
  $R_{C1}$ is a first calibration resistor;
  $R_{C2}$ is a second calibration resistor;
  $C_{R\_C1}$ is a point, in a complex plane of admittance, corresponding to the measurement of a complex value (of impedance or admittance) of the first calibration resistor $R_{C1}$;
  $C_{R\_C2}$ is a point, in said complex plane of admittance, corresponding to the measurement of a complex value (of impedance or admittance) of the second calibration resistor $R_{C2}$.

The measuring device comprises, for example, a current measurement circuit.

The invention also relates to a vehicle steering wheel provided with the previously defined capacitive detection device.

The invention likewise relates to a motor vehicle seat provided with the previously defined capacitive detection device.

The invention further relates to a motor vehicle comprising a steering wheel and/or a seat as defined above.

Other features and advantages of the present invention will be seen more clearly from the following detailed description of an embodiment of the invention provided by way of a non-limiting example and illustrated by the appended drawings, wherein:

FIG. 6.1 shows a flow chart of steps of an initial calibration operation;

FIG. 6.2 shows a flow chart of steps of an operation to measure a sought complex value, of admittance or impedance, between a detection electrode and the frame ground of the vehicle;

The invention is described below, by way of illustrative example, in the context of a capacitive detection device mounted on the steering wheel of a vehicle, said device being intended for detecting the presence of a driver on the steering wheel.

Figure 1:
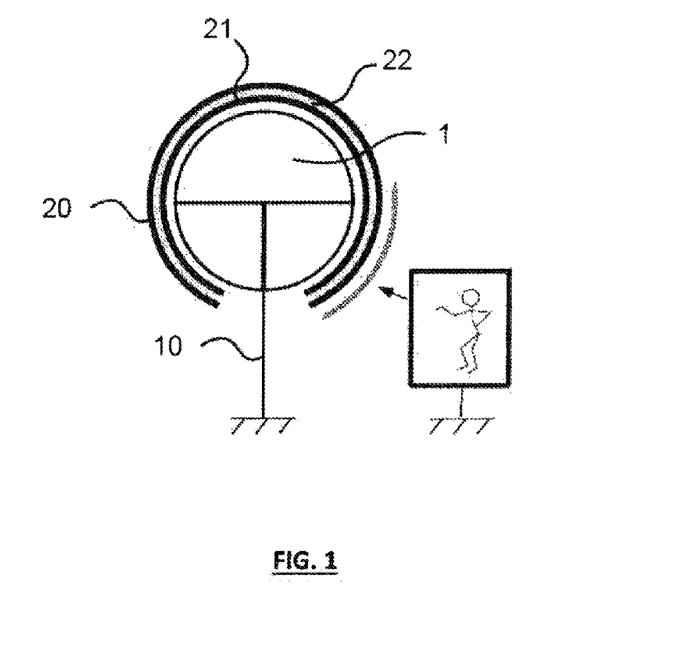
FIG. 1 shows a schematic diagram showing a steering wheel provided with two electrodes for detecting the presence of a driver on the steering wheel, according to a first specific embodiment of the invention.

FIG. 1 schematically shows a steering wheel 1 provided with an armature 10 which can be connected to a frame ground of the vehicle. According to the invention, the steering wheel is provided with an external electrode 20, referred to as "detection electrode", and an internal electrode 21, referred to as "guard electrode", separated by a layer of dielectric material 22. Electrode 21 is present between electrode 20 and the armature 10 of the steering wheel 1. Electrode 21 is present on the steering wheel and is not in direct contact (i.e. in direct electrical contact) with the armature of the steering wheel. Said electrodes 20, 21 and the dielectric material form an element or capacitive sensor having a capacitor C1 of predetermined construction. The capacitance C1 is generally comprised between 500 pF and 10 nF, preferably between 1 nF and 5 nF and even more preferably between 1 nF and 3 nF. This capacitor is visible in FIG. 2.

When the driver of the vehicle touches or moves their hands or a finger towards the steering wheel, a complex impedance $Z_x$, corresponding to a capacitor $C_x$ and a resistor $R_x$ arranged in parallel, is added between the detection electrode 20 and the frame ground of the vehicle. This complex impedance $Z_x$ is a function of the surface area of the organ moved towards the steering wheel. Determining this value thus makes it possible to detect the presence or the absence of a driver on the steering wheel (or close to same).

Figure 2:
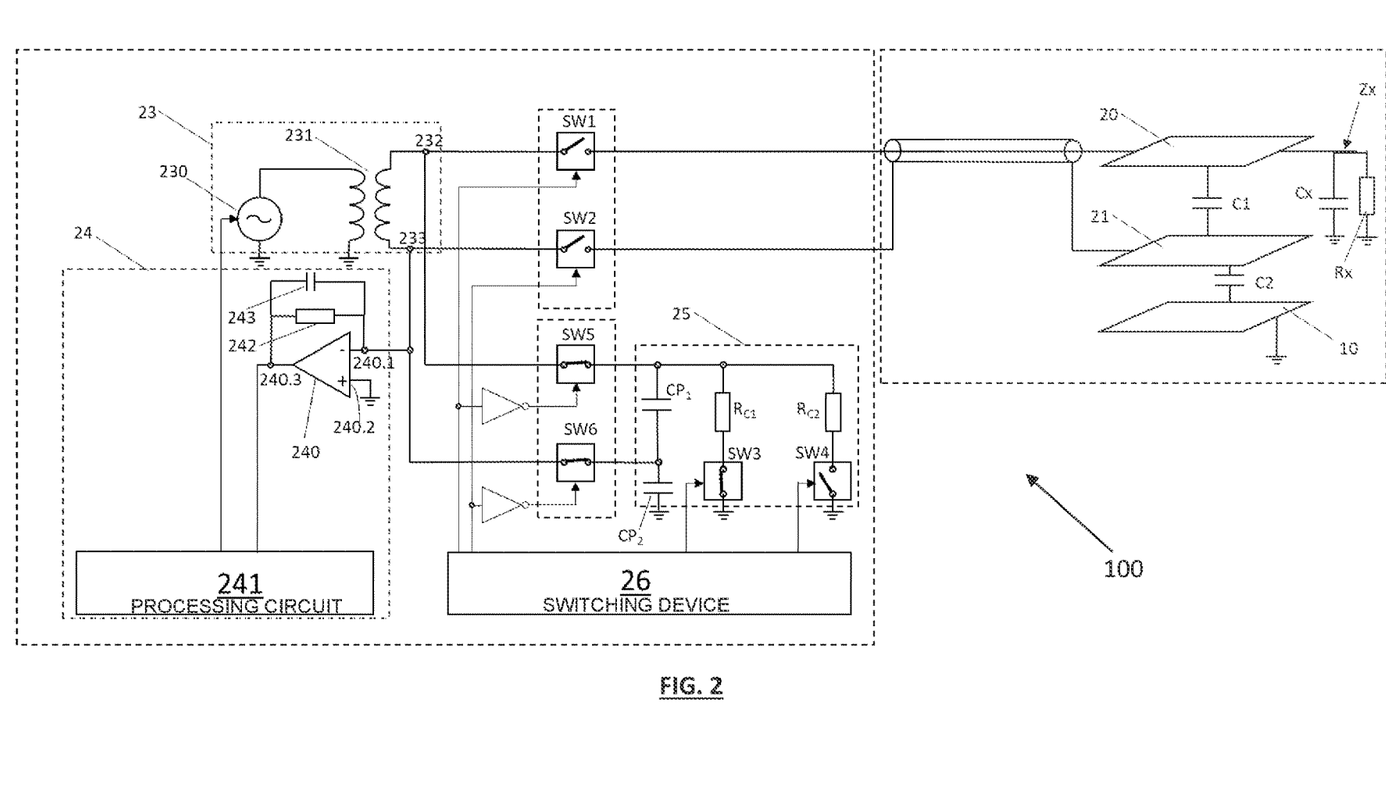
FIG. 2 shows a wiring diagram of a capacitive detection device according to a first embodiment of the invention.

FIG. 2 shows a capacitive detection device 100 according to a specific embodiment of the invention. This device 100 comprises:
- the detection electrode 20 coupled to the guard electrode 21,
- a voltage source 23 arranged to supply an alternating voltage,
- a device 24 for measuring a complex value of impedance or admittance,
- a calibration device 25 comprising at least one calibration resistor, in this case two calibration resistors $R_{C1}$, $R_{C2}$ and
- a switching device 26, SW1-SW6.

FIG. 2 likewise shows various capacitors present at the steering wheel 1:
- the capacitor with construction C1 present between electrodes 20 and 21;
- a capacitor with construction C2 present between the guard electrode 21 and the armature of the steering wheel 10, herein connected to the frame ground of the vehicle; and
- an unknown capacitor (to be determined) $C_x$ present herein between the detection electrode 20 of the steering wheel 1 and the frame ground of the vehicle; this capacitor $C_x$ includes the capacitance added by the hands or finger(s) of the driver on the steering wheel 1 and, where applicable, one or more leakage capacitances linked to the construction of the steering wheel 1; it shows the capacitive portion of the sought complex impedance $Z_x$ between the detection electrode 20 and the frame ground.

The voltage source 23 comprises an alternating voltage generator 230 which herein is connected to a voltage transformer 231. The voltage generator 230 is connected to the primary of the transformer 231. The secondary of the transformer 231 is connected to two output terminals 232 and 233 in order to connect the voltage source 23 to an external component to be supplied with an alternating voltage signal, via the transformer 231. The transformer 231 creates a galvanic isolation between the voltage generator 230 and the connected external component, and prevents the propagation of common mode effects towards the connected component. Alternatively, the voltage transformer could be removed. The switching device herein comprises different relays or electrical switches SW1 to SW6 and a control unit 26. Typically, at the command of the control unit 26, the relays are arranged to
- connect the voltage source 23 to at least one of the electrodes 20 or 21, in measurement mode,
- connect the voltage source 23 to at least one calibration resistor $R_{c1}$, $R_{c2}$ and disconnect the one or more electrodes 20 or 21 from the voltage source 23, in calibration mode.

In the embodiment described herein, the relays SW1 to SW6 have the more precise role of selectively connecting the voltage source 23
- either to the detection electrode 20, in measurement mode;
- or to the calibration device 25, in calibration mode.

The opening and the closing of the various relays SW1 to SW6 are controlled by the control unit 26 in order to obtain the electrical configurations mentioned above in measurement mode and in calibration mode. In particular, in calibration mode, the voltage source 23 must be connected to the calibration device 25 and disconnected from the electrode (herein from the detection electrode 20); SW1 and SW2 are open and SW5 and SW6 are closed. In the specific example described herein, in measurement mode, the voltage source 23 is connected to the electrode (herein the detection electrode 20) and disconnected from the calibration device 25; SW1 and SW2 are closed and SW5 and SW6 are open. However, it could be contemplated to maintain the connection between the voltage source 23 and the calibration device 25 in measurement mode.

The term "measurement mode" is understood to refer to an electrical configuration of the capacitive detection device 100 that is suitable for measuring the complex value of impedance or admittance between one of the electrodes, for example the detection electrode 20, and an electrical circuit reference point. This electrical circuit reference point is, for example, the frame ground of the vehicle. Alternatively, the reference point may be another electrical circuit point, for example the other electrode of the capacitive device.

The term "calibration mode" is understood to refer to an electrical configuration of the capacitive detection device 100 that is suitable for measuring the complex value of impedance or admittance of one or more calibration resistors (herein $R_{C1}$ or $R_{C2}$ or optionally an infinite resistor equivalent to an open circuit, as explained hereunder).

The control unit 26 is, for example, a microcontroller unit (MCU).

In the specific embodiment described herein, the detection electrode 20 is connected to the voltage source 23 via the relay SW1. More specifically, in the embodiment described herein in reference to FIG. 2, the detection electrode 20 is connected to the terminal 232 of the secondary of the transformer 231 via the relay SW1. The guard electrode 21 is connected to the terminal 233 of the secondary of the transformer 231 via the relay SW2. In measurement mode, the two relays SW1 and SW2 are closed in order to connect the output terminals 232 and 233 of the transformer 231 to the detection electrode 20 and to the guard electrode 21, respectively. In calibration mode, the two relays SW1 and SW2 are open to disconnect the voltage source 23 from the electrodes 20 and 21.

The measuring device 24 is arranged to measure a complex value, corresponding to an impedance or an admittance, between an electrode and an electrical circuit reference point. For example, the measuring device 24 is intended for measuring a sought complex impedance "$Z_x$" (or an admittance $1/Z_x$) between the detection electrode 20 and the frame ground of the vehicle. This complex impedance $Z_x$ (or admittance $1/Z_x$) is an unknown impedance (or admittance), to be determined so as to detect the presence or absence of the hands of a person on the steering wheel. When a person, typically a driver, has their hands (or a single hand or else one finger or several fingers on the steering wheel), the complex impedance $Z_x$ comprises a real portion of resistance $R_x$ and an imaginary portion of capacitance $C_x$. Alternatively, the complex admittance $1/Z_x$ comprises a real portion of conductance and an imaginary portion of susceptance.

The measuring device 24 comprises herein a current measurement circuit 240, 242-243 and a processing circuit 241.

The current measurement circuit 240, 242-243 comprises an operational amplifier 240 having a negative input terminal (−) 240.1, a positive input terminal (+) 240.2 and an output terminal 240.3. The positive input terminal (+) 240.2 is connected to a frame ground or to an equivalent voltage signal. The negative input terminal 240.1 is intended for receiving an electric current to be measured for the purpose of measuring a complex impedance or admittance. The output terminal 240.3 of the operational amplifier 240 is linked to the negative input terminal 240.1 via a resistor 242 mounted in parallel with a capacitor 243 so that the operational amplifier 240 forms a current-voltage converter filtered by the capacitor 243.

The value of the resistor 242 is for example comprised between 1 kΩ and 10 kΩ, preferably between 1 kΩ and 5 kΩ The value of the resistor is advantageously selected so that the electromagnetic compatibility tests do not saturate the input stage of the amplifier. The capacitance of the capacitor 243 is selected as a function of the desired pass-band in relation to the frequency of the sine-wave voltage generator. For example, for a frequency of 100 kHz and a 2 kΩ resistor 242, the capacitance of the capacitor 243 is of the order of 220 pF.

The voltage between the input terminals of the operational amplifier 240 is zero or almost zero and its input impedance is very high and considered to be infinite. In this way, the guard electrode 21 constitutes a virtual ground, which removes all impact of the capacitor C2 (between the guard electrode 21 and the frame ground of the vehicle) on the measurement since the voltage at the terminals of the capacitor C2 is zero.

Since the operational amplifier 240 is mounted as a current-voltage converter, the voltage present at the output thereof represents the current circulating through the negative input terminal 240.1 of the operational amplifier 240. In other words, the output voltage of the amplifier 240 is a replica of the current circulating through the negative input terminal 240.1.

The processing circuit 241 is arranged to determine a complex value of impedance or admittance from the output voltage of the operational amplifier 240, representative of the current circulating through the input terminal 240.1. It makes it possible to determine the complex impedance $Z_x$ (or the complex admittance $1/Z_x$), herein between the detection electrode 20 and the frame ground of the vehicle, as well as the complex impedance (or the complex admittance) of one or more calibration resistors (herein $R_{C1}$, $R_{C2}$ or optionally infinite resistor).

Figure 3:
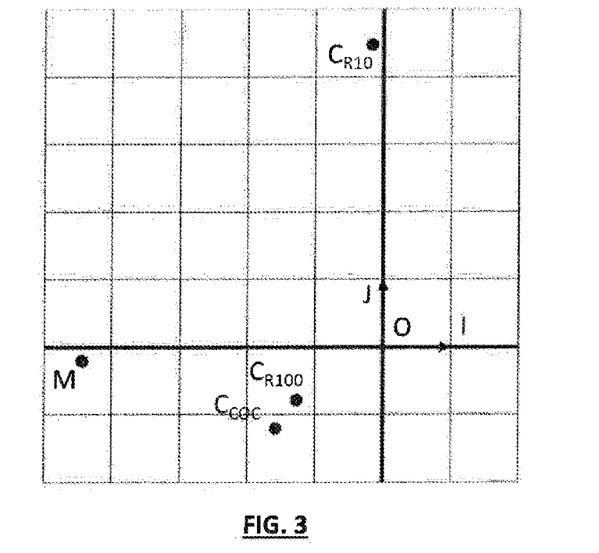
FIGS. 3, 4 and 5 show a complex plane, in this case a complex plane of admittance, comprising an orthonormal coordinate system $(O, \vec{I}, \vec{J})$ on which raw (uncorrected) measurement points, corrected measurement points and calculated points are shown.

A measurement of a complex value of impedance or admittance can be represented in a complex plane such as the one that is shown in FIG. 3. This FIG. 3 shows, by way of illustrative example, a complex plane of admittance comprising an orthonormal coordinate system $(O, \vec{I}, \vec{J})$ wherein $\vec{I}$ and $\vec{J}$ are, respectively, a vector defining an axis of the conductances $1/R$ and a vector defining an axis of the susceptances $C \times 2\pi \times f$ (wherein f is the frequency generated in hertz by the DDS (Direct Digital Synthesis) of the processing circuit 241).

The measurement electronics (voltage source, transformer, OP AMP amplifier, etc.), the connection cables and the environmental conditions, in particular the temperature, have interfering effects on the measurement of complex impedance. In order to compensate for these interfering effects or the performance variations linked to the variabilities of the components, the capacitive detection device 100 is arranged to calibrate or correct a measurement of a complex value of impedance or admittance taken during the operation of the device 100 in measurement mode by means of the calibration device 25.

The calibration device 25 herein comprises two calibration resistors $R_{c1}$ and $R_{c2}$. In the specific embodiment described herein, the two calibration resistors $R_{c1}$ and $R_{c2}$ are different from one another.

The calibration resistors $R_{c1}$ and $R_{c2}$ are advantageously calibrated, i.e. provisioned, and have resistive values determined to guarantee a precise calibration of the measurement in relevant ranges of values to measure the impedance or the admittance of at least one hand or at least one finger on the steering wheel. For example, the calibration resistors $R_{c1}$ and $R_{c2}$ are provisioned to correspond to two hands placed on the steering wheel and to one finger placed on the steering wheel, respectively. In other words, the calibration resistor $R_{c1}$ is provisioned to be substantially equal (by approximation) to a theoretical impedance added by two hands placed on the steering wheel, made up of a capacitance $C_{150}$ of the order of 150 pF. For an arbitrary frequency f of 100 kHz, this theoretical impedance $C_{150}\ Z_{150\ pF}$ is determined by the following equation:

$$Z_{150pF} = \frac{1}{C_{150} \cdot 2\pi f} = 10.610 \text{ kohms.}$$

Since this theoretical value is rounded to 10 kiloohms, the calibration resistor $R_{c1}$ chosen herein is a resistor with a precision of 10 K (10 kiloohms). Similarly, the calibration resistor $R_{c2}$ is provisioned to be substantially equal (by approximation) to the theoretical impedance added by one finger placed on the steering wheel, made up of a capacitance of $C_{15}$ of the order of 15 pF. For an arbitrary frequency f of 100 kHz, this theoretical impedance $Z_{15\ pF}$ is determined by the following equation:

$$Z_{15pF} = \frac{1}{C_{15} \cdot 2\pi f} = 106.10 \text{ kohms.}$$

Since this theoretical value is rounded to 100 K (100 kiloohms), the calibration resistor $R_{c2}$ chosen herein is a resistor with a precision of 100 K (100 kiloohms). The values of the calibration resistors $R_{c1}$ and $R_{c2}$ can, however, be different from 10 K and 100 K, advantageously comprised between 1 K and 200 K, preferably between 5 K and 150 K. The value of the resistor $R_{c1}$ is for example comprised between 1 kΩ and 20 kΩ, preferably between 5 kΩ and 15 kΩ The value of the resistor $R_{c2}$ is for example comprised between 10 kΩ and 200 kΩ, preferably between 50 kΩ and 150 kΩ The calibration resistors make it possible to create frames of reference for measuring a complex value of impedance or admittance. Preferably, precision resistors are used in order to obtain a very low temperature drift (25 ppm), a very good tolerance (0.1%), a better resistance to mechanical stress, a better resistance to moisture and in production during a passage through a furnace. For example, the calibration resistors are obtained by "thin film" technology.

The two calibration resistors $R_{c1}$ and $R_{c2}$ are herein mounted in parallel. Each of the resistors $R_{c1}$ ($R_{c2}$) is connected as follows, at its two terminals, respectively:

to the voltage source 23, via a common electric relay or switch SW5; specifically in the embodiment described herein in reference to FIG. 2, the two resistors $R_{c1}$ ($R_{C2}$) are connected to the output terminal 232 of the transformer 231 via the relay SW5;

to the frame ground of the vehicle, via an individual electric relay or switch SW3 (SW4).

In the specific embodiment described herein, the calibration device 25 likewise comprises a pair of two protective capacitors $C_{P1}$ and $C_{P2}$ mounted in series. The pair of capacitors $C_{P1}$ and $C_{P2}$ in series is mounted in parallel with the calibration resistors $R_{c1}$ and $R_{c2}$ and connected to the frame ground of the vehicle. These capacitors $C_{P1}$ and $C_{P2}$ make it possible to protect the calibration resistors, which herein are precision resistors that are more sensitive than conventional resistors to the effects of ESD (electrostatic discharge). They are provisioned in capacitance ranges close to the design capacitances C1 and C2. More specifically, the capacitance $C_{P1}$ is of the order of the capacitance C1 and the capacitance $C_{P2}$ is of the order of the capacitance C2. More specifically, $C_{P1}$ is comprised between 500 pF and 500 nF, preferably equal to nF, and $C_{P2}$ is comprised between 100 pF and 10 nF, preferably equal to 1 nF. Thanks to this, the current measured during a calibration is similar to a current measured during a measurement of the sought impedance $Z_x$ (or admittance $1/Z_x$). This results in an optimal measurement precision.

The calibration resistor $R_{c1}$ coupled in series with the relay SW3, the calibration resistor $R_{c2}$ coupled in series with the relay SW4 and the pair of capacitors $C_{P1}$ and $C_{P2}$ in series form three circuit branches connected in parallel between the alternating voltage source 23 (in this case the output terminal 232 of the transformer 231), via the relay SW5, and the frame ground of the vehicle.

The switching device likewise comprises a relay SW6 inserted between the output terminal 233 of the transformer 231 and a connection point between the two protective capacitors $C_{P1}$ and $C_{P2}$. Thus, in calibration mode, the protective capacitor $C_{P1}$ is connected at its terminals to the two output terminals 232 and 233 of the secondary of the transformer 231, via the first relay SW5 and the second relay SW6, respectively. The protective capacitor $C_{P2}$ is connected at its two terminals to the output terminal 233 of the secondary of the transformer 231 and to the frame ground, respectively, via the relay SW6.

The measurement circuit 24 is intended for receiving a current signal representative of an impedance or an admittance to be measured herein through the negative input terminal 240.1 of the amplifier 240. To this end, the switching device is arranged to connect the input terminal 240.1 either to the branch connecting the output terminal 233 of the current source 23, in measurement mode, or to the connection point between the two protective capacitors $C_{P1}$ and $C_{P2}$ via the relay SW6. In the embodiment of FIG. 2, the negative input terminal 240.1 of the amplifier 240 is connected to a connection branch linking the relay SW6 and the output terminal 233 of the transformer 231. In the event that the capacitors $C_{P1}$ and $C_{P2}$ are not used, the negative input terminal 240.1 of the amplifier 240 is connected only to the output terminal 233 of the transformer 231, and the resistors $R_{C1}$ and $R_{C2}$ in turn are connected directly to the output terminal 232 of the transformer 231.

Figure 4:
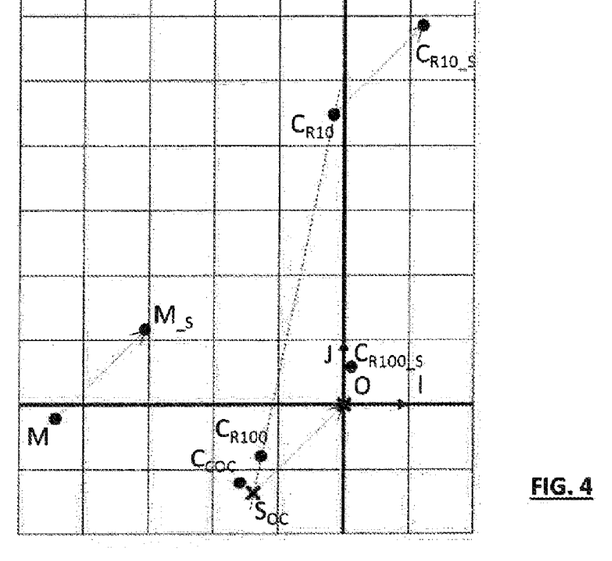
Figure 5:
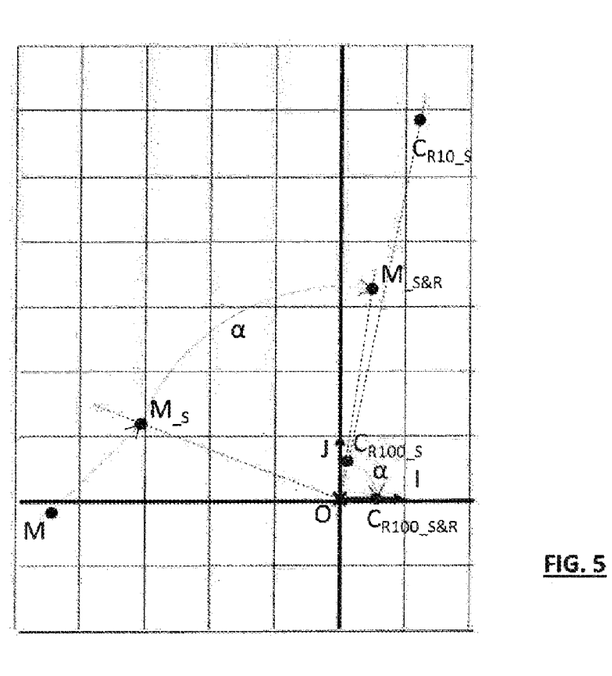

The following is a description of a method for detecting a person on the steering wheel 1 of the vehicle, corresponding to the operation of the capacitive calibration device 100, in reference to the graphs in FIGS. 3 to 5 and to the flow charts in FIGS. 6.1 and 6.2.

The present invention makes it possible to calibrate (or correct) measurements of complex values of impedance or admittance herein between the detection electrode and the frame ground from calibration resistors $R_{c1}$ and $R_{c2}$ having known resistive values that are herein different from one another. The calibration resistors $R_{c1}$ and $R_{c2}$ are used to take calibration measurements. These calibration measurements can be repeated to update the calibration continuously, as will be described below.

Figure 61:
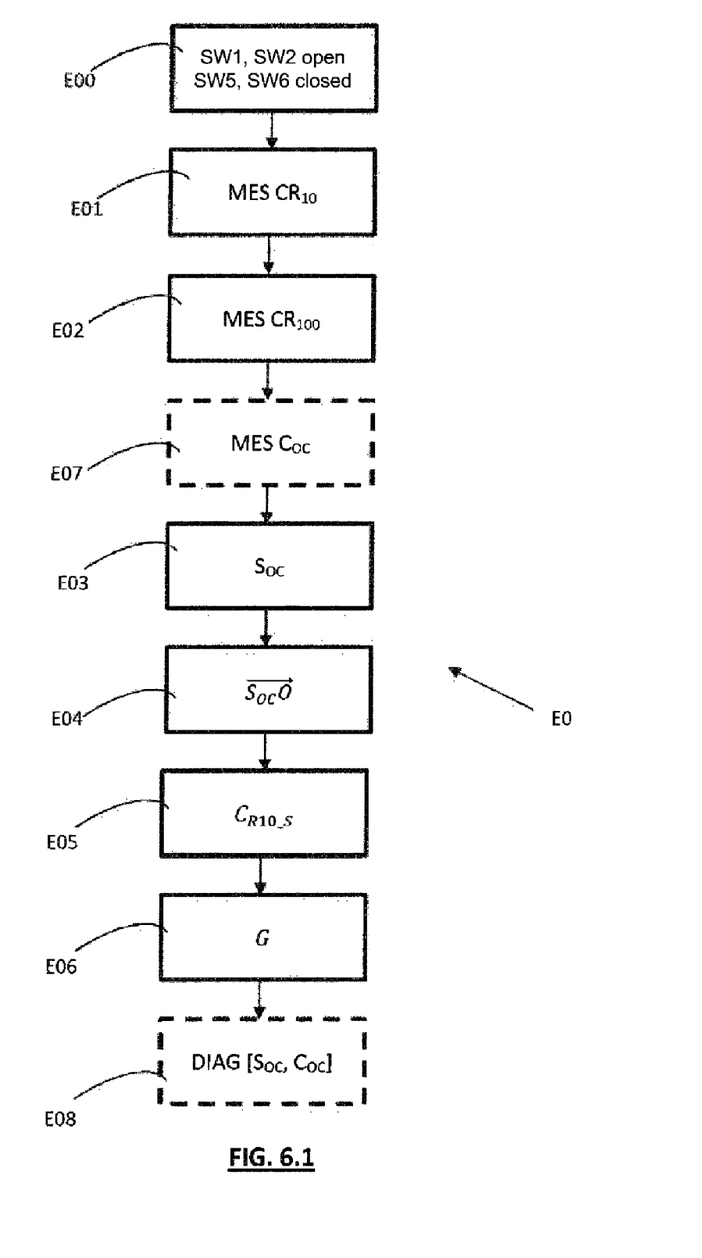
Figure 62:
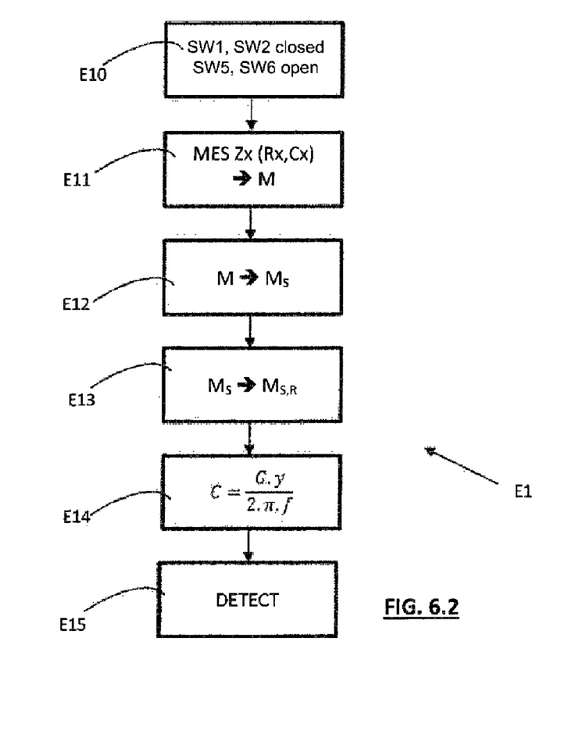

The detection method comprises an initial calibration operation E0, shown in FIG. 6.1. This initial calibration operation E0 aims to measure the complex value of impedance or admittance of each of the calibration resistors and likewise herein an open-circuit complex value of impedance or admittance equivalent to the complex impedance or admittance of an infinite resistor. It comprises a first step E00 of configuration in calibration mode of the capacitive detection device 100. During this step E00, at the command of the control unit 26, relays SW1 and SW2 are open and relays SW5 and SW6 are closed. The voltage source 23 is then disconnected from the electrodes 20, 21 and connected to the calibration device 25 so as to supply alternating voltage to the calibration stage, herein through the pair of protective capacitors $C_{P1}$ and $C_{P2}$.

In this configuration of the detection device 100 (SW1-SW2 open and SW5-SW6 closed), the calibration resistors $R_{c1}$ and $R_{c2}$ are connected one after the other (separately) to the voltage source 23 in order to take two measurements of complex value of impedance or admittance of the resistor $R_{c1}$ and of the resistor $R_{c2}$, respectively. Thus, the switching device is arranged to connect the voltage source 23 selectively to a first one of the two resistors Rei, and then to a second one of the two resistors $R_{c2}$. More precisely, since the relay SW3 is closed and the relay SW4 is open, the measuring device 24 measures the complex impedance or admittance of the calibration resistor $R_{c1}$, during a first calibration measurement step E01. Then, since the relay SW3 is open and the relay SW4 is closed, the measuring device 24 measures the complex impedance or admittance of the calibration resistor $R_{c2}$, during a second calibration measurement sub-step E02. In FIGS. 3 to 5, points $C_{R10}$ and $C_{R100}$ represent, in the complex plane which herein is of admittance $(O, \vec{I}, \vec{J})$, the raw measurement of the complex value of admittance of the calibration resistor $R_{C1}$ and the raw measurement of the complex value of admittance of the calibration resistor $R_{C2}$, respectively. "Raw measurement" is understood to refer to an uncorrected measurement. Steps E01 and E02 can be carried out in any given order.

During a subsequent step E03, the processing circuit 241 calculates herein the theoretical open-circuit admittance $S_{OC}$ of the detection device 100, in other words the admittance of an infinite calibration resistor (replacing for example $R_{c1}$ or $R_{c2}$), from measurements of complex value (of impedance or admittance) of the two calibration resistors $R_{c1}$ and $R_{C2}$, according to the following equation:

$$\overrightarrow{S_{OC}C_{R10}} = 10 \times \overrightarrow{S_{OC}C_{R100}} \tag{1}$$

The equation (1) translates the following mathematical properties:
- the admittances $S_{OC}$, $C_{R10}$ and $C_{R100}$ are aligned in the complex plane of admittance since all three represent only resistances and
- there is a proportionality factor 10 between the amplitude of the admittance $C_{R10}$ relative to the open-circuit admittance $S_{OC}$ and the amplitude of the admittance $C_{R100}$ relative to the open-circuit admittance $S_{OC}$.

In the complex plane $(O, \vec{I}, \vec{J})$, by definition, the theoretical infinite impedance point $S_{OC}$ is considered to be the origin O of the orthonormal coordinate system. And yet, as shown in FIGS. 3 and 4, due to the previously mentioned interfering effects, the point $S_{OC}$ and the origin O of the coordinate system $(O, \vec{I}, \vec{J})$ do not coincide in the complex plane $(O, \vec{I}, \vec{J})$. The translation which sends the point $S_{OC}$ onto the origin O of the complex plane $(O, \vec{I}, \vec{J})$ defines a vector $\overrightarrow{S_{OC}O}$. The translation characterized by the vector $\overrightarrow{S_{OC}O}$ defines a first offset correction to be applied to a measurement taken by the measuring device 24. During a step E04, the processing circuit 241 calculates the offset or translation vector $\overrightarrow{S_{OC}O}$.

During a step E05, the processing circuit 241 applies to at least one of the two measurements of complex value of impedance or admittance of the resistors $R_{c1}$ and Rea a first correction corresponding to a translation according to the vector $\overrightarrow{S_{OC}O}$ of the point $C_{R10}$ (or $C_{R100}$) in the complex plane $(O, \vec{I}, \vec{J})$. The image point of the point $C_{R10}$ (or $C_{R100}$) by the translation according to the vector $\overrightarrow{S_{OC}O}$ is an offset point $C_{R10\_S}$ (or $C_{R100\_S}$) in the complex plane $(O, \vec{I}, \vec{J})$, as shown in FIG. 4. It complies with the following equation:

$$\overrightarrow{C_{R10}C_{R10\_S}} = \overrightarrow{S_{OC}O} \tag{2}$$

During a step E06, the processing circuit 241 calculates a gain G for conversion into standard units of measurement—siemens and farad, respectively—of the conductances and the capacitances. The conversion gain G is calculated according to the following equation:

$$G = \frac{|R_{100\Omega} - R_{10\Omega}|}{R_{100\Omega} \times R_{10\Omega} \times \|C_{R10}C_{R100}\|} = \frac{9 \cdot 10^4}{10^9 \times \|C_{R10}C_{R100}\|} = \frac{9}{10^5 \times \|C_{R10}C_{R100}\|} \tag{3}$$

The above equation (3) results from the fact that the difference between the respective admittances of the two calibration resistors $R_{c1}$ and $R_{c2}$ is equal to the gain G multiplied by the norm of the vector connecting the measurement point $C_{R10}$ and the measurement point $C_{R100}$. In other words:

$$\frac{1}{R_{10\Omega}} - \frac{1}{R_{100\Omega}} = G \times \|\overrightarrow{C_{R10}C_{R100}}\|.$$

The method can likewise comprise a measurement of an open-circuit complex value of impedance or admittance, taken for example during the initial calibration operation E0 after the measurements E01 and E02 of impedance of the calibration resistors $R_{c1}$ and $R_{c2}$, during a step E07 (shown in dotted lines in FIG. 6.1). This open-circuit complex value of impedance or admittance corresponds to the impedance or admittance of a calibration resistor but with an infinite resistive value. Note $C_{OC}$, the point of the plane of admittance $(O, \vec{I}, \vec{J})$ corresponding to the measurement of the open-circuit complex value of admittance, as shown in FIGS. 3 and 4. During correct operation of the detection device 100, the point $C_{OC}$ is close to the calculated theoretical point $S_{OC}$, as shown in FIG. 4. An excessive offset between $C_{OC}$ and $S_{OC}$ indicates a malfunction of the capacitive detection device 100. The method optionally comprises a step E08 of diagnosing correct operation, during which the processing circuit 241 verifies whether the measured point $C_{OC}$ is close to the calculated theoretical point $S_{OC}$ in order to detect the correct or incorrect operation of the detection device 100. For example, the distance between the two points $C_{OC}$ and $S_{OC}$ is calculated and compared with a limit (or threshold) value. If the calculated distance is less than the limit value, the operation is considered to be correct. If the calculated distance is more than the limit value, a malfunction of the detection device 100 is detected. In this case, a warning signal may be transmitted to the driver of the vehicle.

The calibration operation E0 is followed by an operation E1 of measuring the impedance between the detection electrode 20 and the frame ground of the vehicle. When a driver has their hands on the steering wheel (or else only one or more fingers), they add an impedance $Z_x$ comprising a resistance $R_x$ and a capacitance $C_x$ in parallel between the detection electrode 20 and the frame ground, as shown in FIG. 2.

The measurement operation E1 comprises a first step E10 of configuration in measurement mode of the capacitive detection device 100. During this step E10, at the command of the control unit 26, the relays SW1 and SW2 are closed and the relays SW5 and SW6 are herein open. The voltage source 23 is then connected to the electrodes 20, 21, the detection electrode 20 being connected to the output terminal 232 of the voltage source, and disconnected from the calibration device 25 so as to supply the detection electrode 20 with alternating voltage. In this configuration, the relays SW3 and SW4 are advantageously open.

During a measurement step E11, the detection electrode 20 receives an alternating voltage signal and the measurement circuit 24 measures the electric current circulating through the guard electrode 21 by means of the amplifier 240. The processing circuit 241 determines a complex value of impedance $Z_x$ or admittance $1/Z_x$ between the detection electrode 20 and the frame ground. FIG. 4 shows herein in the complex plane of admittance $(O, \vec{I}, \vec{J})$ a measurement point M representing the measurement of a complex value of impedance $Z_x$ or admittance $1/Z_x$ as well as the offset measurement point $C_{R10\_S}$ of the resistor $R_{C1}$, the origin O and the calculated point $S_{OC}$ corresponding to an infinite (or open-circuit) impedance.

During a subsequent step E12, the processing circuit 241 applies to the measurement of the complex value of impedance $Z_x$ or admittance $1/Z_x$ a first correction corresponding to a translation by the vector $\overrightarrow{S_{OC}O}$ of the measurement point M in the plane of admittance $(O, \vec{I}, \vec{J})$. The image point of the measurement point M by this translation is an offset point Ms in the plane of admittance $(O, \vec{I}, \vec{J})$. It complies with the following equation:

$$\overrightarrow{MM_S} = \overrightarrow{S_{OC}O} \qquad (4)$$

The calibration resistors $R_{C1}$, $R_{C2}$ are pure resistors that have real (resistive) values. By convention, the resistors are represented in the complex plane, herein of admittance $(O, \vec{I}, \vec{J})$, by points on the conductance axis $(O, \vec{I})$. On the basis of this geometric property and at least two of the points representing the measured complex values of the resistors $R_{C1}$, $R_{C2}$ and the calculated open-circuit complex value of impedance or admittance (namely $C_{R10}$, $C_{R100}$ and $S_{OC}$ before correction by offset or else $C_{R10\_S}$, $C_{R100\_S}$ and O after offset by $\overrightarrow{S_{OC}O}$), the processing circuit 241 applies to the offset measurement point $M_S$ a phase correction in the complex plane during a step E13, for example by the following equations:

$$\|\overrightarrow{OM_S}\| = \|OM_{\_S\&R}\| \qquad (5)$$

$$\alpha = (\overrightarrow{OM_S}, \overrightarrow{OM_{\_S\&R}}) = (\overrightarrow{OC_{R10,S}}, \overrightarrow{OI}) \qquad (6)$$

wherein $K_{\_S\&R}$ is the measurement point M after offset correction and phase correction.

In a more general way, said phase correction corresponds to a rotation according to an angle $\alpha$ between:

a straight line defined by two points of the complex plane (of admittance $(O, \vec{I}, \vec{J})$ or of impedance), obtained from measurements of complex values of impedance or admittance of the resistors (calibration resistor(s) and/or infinite resistor) and the axis $(O, \vec{I})$ of the conductances or resistances of the complex plane.

The two points of the complex plane $(O, \vec{I}, \vec{J})$ obtained from measurements of complex values of impedance or admittance of resistors can be selected among one of the following two groups of points:

$C_{R10}$, $C_{R100}$ and $S_{OC}$,
$C_{R10\_S}$, $C_{R100\_S}$ and O,
or for example $C_{R10}$ and $C_{OC}$ The processing circuit thus determines a complex value (of impedance or admittance) corrected by offset and phase correction, represented herein by the point $K_{\_S\&R}$ in the plane of admittance $(O, \vec{I}, \vec{J})$. Note x and y as the abscissa and ordinate coordinates of the point $M_{\_S\&R}$ in the plane of admittance $(O, \vec{I}, \vec{J})$.

The offset correction and the phase correction can be carried out in any given order provided that the calculations are suitable.

During a scaling step E14, the processing unit 241 scales the x and y coordinates of the point $M_{\_S\&R}$ in order to convert them into ohm and farad units of measurement, respectively, according to the following equations:

$$C = \frac{G \cdot y}{2 \cdot \pi \cdot f} \qquad (7)$$

$$R = \frac{1}{G \cdot x} \qquad (8)$$

wherein f is the frequency in hertz generated by the DDS (Direct Digital Synthesis) of the processing integrated circuit 241.

During a final step E15, the processing unit 241 detects the presence or the absence of a driver on the steering wheel 1 using the capacitance value C obtained during step E14. This capacitance value C makes it possible to assess the surface of the hand or finger in contact with the steering wheel 1. A capacitance of the order of pF corresponds to one finger placed on the steering wheel 1. A capacitance of the order of 150 pF corresponds to two hands placed on the steering wheel 1.

Figure 7:
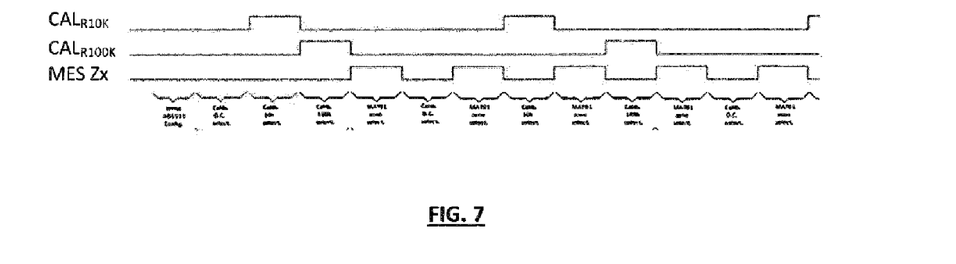
FIG. 7 shows a sequence of measurements of the sought complex value interlaced with measurements of complex values (of impedance or admittance) of two calibration resistors shown in FIG. 2.

In a specific embodiment of the invention, following the execution of the initial calibration operation E0 followed by the operation E1 to measure impedance $Z_x$, the step E11 of measuring a complex value of impedance $Z_x$ (or admittance $1/Z_x$) is repeated cyclically and, between two measurements of $Z_x$ (or $1/Z_x$), calibration steps (E01, E02 and/or E07) are repeated. The sought measurements of impedance (or admittance) $Z_x$ (or $1/Z_x$) are thus interlaced with calibration measurements in order to guarantee a continuous calibration for the entire duration of the detection on the steering wheel 1. For example, half of the measurements are dedicated to measurements of impedance $Z_x$ (or admittance $1/Z_x$) in measurement mode and the other half of the measurements are dedicated to calibration measurements (E01, E02 or E07) in calibration mode in order to update the calibration data gradually and continuously over time. FIG. 7 shows an example of an embodiment of this interlacing of the measurements of $Z_x$ and the calibration measurements. The first and second lines show the measurements of impedances of the resistors $R_{C1}$ and $R_{C2}$, respectively. The last line shows the measurements of impedance $Z_x$ (or admittance $1/Z_x$). Initially, as described in reference to FIG. 6.1, the detection device 100 measures a complex value (of impedance or admittance) of the resistor $R_{C1}$ and then measures a complex value (of impedance or admittance) of the resistor $R_{C2}$ in order to obtain a first set of calibration data. Then, a first measurement of impedance $Z_x$ (or admittance $1/Z_x$) is taken. After this initial phase, the measurements of impedance $Z_x$ (or admittance $1/Z_x$) are repeated regularly, according to a predetermined measurement frequency and, between two measurements, a single calibration measurement is taken herein, namely either a measurement of impedance of the calibration resistor $R_{C1}$, or a measurement of impedance of the calibration resistor $R_{C2}$. It is also possible to alternate these calibration measurements with an open-circuit measurement (equivalent to a calibration resistor with infinite value). Thus, the different calibration measurements are taken one after the other cyclically between two consecutive measurements of impedance $Z_x$ (or admittance $1/Z_x$). The calibration measurements are thus interlaced between the measurements of impedance $Z_x$ (or admittance $1/Z_x$).

The interlacing of the measurements of impedance Z, (or admittance $1/Z_x$) and the calibration measurements is advantageously carried out during the entire operating time of the detection device 100, typically from the instant the vehicle is started and until its engine is switched off.

In the preceding description, the capacitive detection device 100 comprises two calibration resistors having resistive values that are different from one another.

In a first alternative embodiment, the capacitive detection device comprises two similar calibration resistors (i.e. having the same resistive value). In this case, switching means are provided in order to produce two different resistive dipoles from the two calibration resistors, which makes it possible to take two measurements of a complex value of impedance (or admittance) and to obtain two separate points for calibration measurement in the complex plane. For example, a first resistive dipole comprises only one of the two calibration resistors and the second resistive dipole comprises the two calibration resistors mounted in parallel or in series.

In a second alternative embodiment, the capacitive detection device comprises a single calibration resistor making it possible to perform a first step of measuring the impedance of a calibration resistor, for example comprised between 10 kn and 100 kn. In this case, the second step of measuring the impedance of another calibration resistor is removed and the method comprises a step of measuring the open-circuit resistance, identical to step E07, in order to obtain an open-circuit impedance measurement. In this case, the two corrections (offset correction and phase correction) to be applied are determined from the point representing the impedance measurement of a calibration resistor in the plane of admittance, for example $C_{R100}$ (if the calibration resistor is of 100 kn) and of the point $C_{OC}$ showing the open-circuit impedance measurement. The open-circuit impedance (or admittance) is, in this case, measured but not calculated theoretically (the point $S_{OC}$ is not calculated).

In the preceding description, the detection electrode is connected to the voltage source 23, in this case to its output terminal 232, via the relay SW1. In an alternative embodiment of the electrical assembly, it is the guard electrode that is connected to the voltage source 23, in this case to its output terminal 232, via the relay SW1.

In the preceding description, the measuring device 24 measures a complex value of impedance or admittance in order to detect the presence or the absence of a person on the steering wheel between an electrode (for example the detection electrode 20) and a frame ground of the vehicle. Alternatively, the impedance measuring device 24 measures a complex value of impedance or admittance in order to detect the presence or the absence of a person on the steering wheel between one of the two electrodes 20, 21 and an electrical circuit reference point. The point of the electrical circuit that constitutes a reference point for the sought complex impedance or admittance measurement can be the other electrode.

The present invention has been described in the context of detecting the presence of a driver on the steering wheel of the vehicle. In another embodiment of the invention, the capacitive detection device is intended for detecting the presence or the absence of a person on a seat of the vehicle. More typically, the invention is applied to the detection of the presence of a person close to or on (i.e. in contact with) a component of a motor vehicle.

The invention claimed is:

1. A capacitive detection device for detecting the presence of a person close to or in contact with a component of a motor vehicle, provided with a capacitive sensor, said device comprising
   at least one electrode of the capacitive sensor,
   a voltage source arranged to supply an alternating voltage,
   a device for measuring a complex value, corresponding to an impedance or an admittance, between said electrode and an electrical circuit reference point;
   a calibration resistor for calibrating the measurement of a complex value of impedance or admittance;
characterized in that
said capacitive detection device comprises a switching device arranged to
   connect the voltage source to said electrode, in measurement mode,
   connect the voltage source to the calibration resistor and disconnect said electrode from the voltage source, in calibration mode,
and the measuring device is arranged to
   measure a first complex value of the calibration resistor, during operation in calibration mode;
   measure a second complex value between said electrode and said electrical circuit reference point, during operation in measurement mode, and
   correct the second measured complex value based on the first measured complex value.

2. The device according to claim 1, characterized in that it comprises two calibration resistors.

3. The device according to claim 2, characterized in that it is arranged to repeat the measurement of the second complex value between said electrode and the electrical circuit reference point cyclically and, between two consecutive measurements of said second complex value, to take a calibration measurement.

4. The device according to claim 2, characterized in that the two calibration resistors have different resistive values.

5. The device according to claim 4, characterized in that a first one of the calibration resistors has a resistive value comprised between 1 kΩ and 20 kΩ and a second one of the calibration resistors has a resistive value comprised between 10 kΩ and 200 kΩ.

6. The device according to claim 4, characterized in that the two calibration resistors are mounted in parallel and the switching device is arranged to connect the voltage source selectively to one or the other of the two resistors.

7. The device according to claim 1, characterized in that the measuring device is arranged to apply an offset correction to the second measured complex value, said offset correction corresponding to a translation according to a vector $\overrightarrow{S_{OC}O}$ in a complex plane, the point SOC being a point of the complex plane corresponding to an open-circuit complex value of admittance or impedance of the capacitive detection device and the point O corresponding to the origin of the complex plane.

8. The device according to claim 7, characterized in that the measuring device is arranged to calculate said open-circuit complex value of impedance or admittance of the capacitive detection device from two complex values measured by means of the two calibration resistors.

9. The device according to claim 8, characterized in that the measuring device is arranged to measure an open-circuit complex value of impedance or admittance and to compare said measured open-circuit complex value of impedance or admittance and said calculated open-circuit complex value of impedance or admittance in order to verify the correct operation of the capacitive detection device.

10. The device according to claim 2, characterized in that the measuring device is arranged to apply a phase correction to the second measured complex value, said phase correction corresponding to a rotation according to an angle α between a straight line defined by two points in a complex plane, obtained from two complex values of impedance or admittance measured by means of the two calibration resistors, and an axis of the resistances or conductances of the complex plane.

11. The device according to claim 1, characterized in that it comprises a pair of protective capacitors in series, said pair of capacitors being mounted in parallel with the one or more calibration resistors and in that one of the two capacitors is connected at its terminals to the voltage source via two respective switches and the other capacitor is connected to a frame ground of the vehicle.

12. The device according to claim 1, characterized in that the measuring device is arranged to calculate a capacitance value between said electrode and the electrical circuit reference point, from said second complex value measured and then corrected, by applying a scaling gain G to the imaginary portion of said second value measured and then corrected, the gain G being provided by the equation $$G = \frac{|R_{C1} - R_{C2}|}{R_{C1} \times R_{C2} \times \|\overline{C_{R\_C1}C_{R\_C2}}\|}$$

wherein
$R_{C1}$ is a first calibration resistor;
$R_{C2}$ is a second calibration resistor;
$C_{R\_C1}$ is a point, in a complex plane of admittance, corresponding to the measurement of a complex value of the first calibration resistor $R_{C1}$;
$C_{R\_C2}$ is a point, in said complex plane of admittance, corresponding to the measurement of a complex value of the second calibration resistor $R_{C2}$.

13. The device according to claim 1, characterized in that the measuring device comprises a current measurement circuit.

14. A motor vehicle steering wheel provided with the capacitive detection device according to claim 1.

15. A motor vehicle comprising a steering wheel according to claim 14.

16. A motor vehicle seat provided with the capacitive detection device according to claim 1.

17. A motor vehicle comprising a seat according to claim 16.

* * * * *